United States Patent [19]

Langdon et al.

[11] Patent Number: 5,500,270
[45] Date of Patent: Mar. 19, 1996

[54] CAPILLARY LAMINATE MATERIAL

[75] Inventors: Fred M. Langdon; William R. Ouellette, both of Cincinnati; John B. Burchnall, West Chester, all of Ohio

[73] Assignee: The Procter & Gamble Company, Cincinnati, Ohio

[21] Appl. No.: 212,487

[22] Filed: Mar. 14, 1994

[51] Int. Cl.$^6$ .............................. A61F 13/15; B32B 3/12; B32B 7/04

[52] U.S. Cl. .................... 428/119; 428/116; 428/118; 428/131; 428/132; 428/133; 428/137; 428/138; 428/166; 428/167; 604/378; 604/383; 604/385.1

[58] Field of Search ................ 428/131, 132, 133, 137, 138, 116, 118, 166, 167, 119; 604/385.1, 378, 383

[56] References Cited

U.S. PATENT DOCUMENTS

| | | | |
|---|---|---|---|
| 3,628,720 | 12/1971 | Schmedding | 229/55 |
| 3,945,386 | 3/1976 | Anczurowski et al. | 128/287 |
| 4,064,300 | 12/1977 | Bhangu | 428/120 |
| 4,276,338 | 6/1981 | Ludwa et al. | 428/137 |
| 4,338,366 | 7/1982 | Evans et al. | 428/76 |
| 4,414,255 | 11/1983 | Tokuyama et al. | 428/154 |
| 4,438,167 | 3/1984 | Schwarz | 428/138 |
| 4,450,195 | 5/1984 | Hagbjer | 428/178 |
| 4,587,152 | 5/1986 | Gleichenhagen et al. | 428/195 |
| 4,636,424 | 1/1987 | Amemiya et al. | 428/198 |
| 4,723,953 | 2/1988 | Rosenbaum et al. | 604/369 |
| 4,808,675 | 2/1989 | Twilley et al. | 525/408 |
| 4,847,142 | 7/1989 | Twilley et al. | 428/252 |
| 4,898,761 | 2/1990 | Dunaway et al. | 428/137 |
| 4,948,653 | 8/1990 | Dinter et al. | 428/172 |
| 5,028,332 | 7/1991 | Ohnishi | 210/500.34 |
| 5,116,661 | 5/1992 | Matsubara | 428/198 |
| 5,154,960 | 10/1992 | Mucci et al. | 428/68 |
| 5,261,899 | 11/1993 | Visscher et al. | 604/367 |
| 5,368,909 | 11/1994 | Langdon et al. | 428/137 |

FOREIGN PATENT DOCUMENTS 0496567  7/1992  European Pat. Off. ........ A61F 13/15

Primary Examiner—D. S. Nakarani
Attorney, Agent, or Firm—Kevin C. Johnson; William Scott Andes; E. Kelly Linman

[57] ABSTRACT

The present invention pertains to a laminate material. The laminate material includes a first sheet and a second sheet spaced apart from one another by spacers to define a capillary zone for the capillary movement of fluid between the first and second sheets. The spacers connect the first sheet and the second sheet together to form the laminate material.

47 Claims, 7 Drawing Sheets

CAPILLARY LAMINATE MATERIAL

TECHNICAL FIELD

The present invention relates to laminate materials, and more particularly the present invention relates to laminate materials having a capillary zone or passageway to acquire, move and/or store fluid within the laminate material. The laminate material of the present invention is particularly suitable for use as a topsheet, an acquisition layer and/or an absorbent core in absorbent articles such as disposable diapers, catamenials, sanitary napkins, bandages, incontinent briefs and the like.

BACKGROUND OF THE INVENTION

It has long been known in the disposable absorbent article art that it is extremely desirable to construct absorptive devices such as disposable diapers, catamenials, sanitary napkins, bandages, incontinent briefs, and the like, presenting a dry surface feel to the user to improve wearing comfort and to minimize the development of undesirable skin conditions due to prolonged exposure to moisture absorbed within the article.

One commercially used solution to the aforementioned problem is the use of a nonwoven web as a topsheet on a disposable absorbent article. The nonwoven web topsheet provides a soft surface in contact with the users skin. Moisture deposited on the nonwoven topsheet is transmitted through the openings between the fibers and into the absorbent core. However, because of the randomness of the fibers within the nonwoven topsheet, some moisture tends to hang up or collect within the nonwoven creating an undesirable condition as the skin is exposed to the moisture within the nonwoven.

Another solution to the aforementioned problem is disclosed in commonly assigned U.S. Pat. No. 4,342,314 issued to Radel et al. on Aug. 3, 1982 and hereby incorporated herein by reference. Radel et al. discloses an absorbent article with a wearer-contacting topsheet comprising a resilient, macroscopically expanded, three-dimensional plastic web exhibiting a combination of fiber-like and plastic properties. In a preferred embodiment, the macroscopically expanded, three-dimensional plastic web topsheet disclosed in Radel et al. exhibits a fine-scale three-dimensional microstructure comprising a regulated continuum of capillary networks, of steadily decreasing size, originating in and extending from one surface of the web and terminating in the form of apertures in the opposite surface thereof to promote rapid fluidtransport in the direction of decreasing capillary size. The web's fiber-likeappearance is comprised of a continuum of fiber-like elements, the opposed ends of each of the fiber-like elements being interconnected to at least one other of the fiber-like elements. A typical capillary network in the Radel et al. structure comprises an uppermost capillary opening or aperture formed by a multiplicity of primary fiber-like elements interconnected to one another in the uppermost plane of the web. The uppermost opening may, if desired, be further subdivided into smaller capillary openings by secondary and tertiary fiber-like elements at planes located below the wearer-contacting surface of the web. Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion and extending generally in the direction of the absorbent pad-contacting surface of the web. The sidewall portions which intersect one another are joined to one another intermediate the wearer-contacting surface and the absorbent pad-contacting surface of the web, thereby forming a capillary network interconnecting the opposed surfaces of the web. The secondary and tertiary fiber-like elements, when employed, are generally similar, but originate in planes below the wearer-contacting surface of the web.

One drawback associated with the use of topsheets comprised of plastic is that despite their superior fluid handling characteristics some users are very reluctant to place a topsheet which they readily perceive as plastic by virtue of its glossy appearance in contact with their skin.

To reduce the gloss on the web's visible surface, i.e., that portion of the web which is visible from directly overhead, it has been learned that inclusion of a microscopic pattern of surface aberrations which are not discernible when the perpendicular distance between the viewer's eye and a plane of the web is about 12 inches is highly effective. Commonly assigned U.S. Pat. No. 4,463,045 issued to Ahr et al. on Jul. 31, 1984 and hereby incorporated herein by reference, s defines the relevant criteria which must be satisfied so that the three-dimensionally expanded web will exhibit a substantially non-glossy visible surface. The topsheet of the type generally disclosed in Radel et al., having surface aberrations according to Ahr et al., exhibits a fiber-like appearance and tactile impression as well as a non-glossy visible surface. In addition, it is highly effective in promoting rapid fluid transfer from the first or wearer-contacting surface to the second or absorbent pad-contacting surface of the topsheet. Topsheets of the latter type have enjoyed wide spread commercial success on catamenial pads due to their clean and dry appearance in use when contrasted to conventional nonwoven fibrous topsheets.

While nonwoven topsheets and plastic topsheets of the type generally disclosed in Radel et al. and Ahr et al. have enjoyed widespread commercial success, it will be readily appreciated that even further improvements in clean and dry appearance in use are highly desirable in products of this type.

SUMMARY OF THE INVENTION

The present invention pertains, in a preferred embodiment, to a capillary laminate material comprised of at least two layers or sheets having a capillary zone between the sheets. The capillary zone between the sheets is established and maintained by at least one spacer element which simultaneously holds the two layers apart and keeps them from separating further. In a preferred embodiment the capillary laminate material includes a plurality of spacer elements. At least one of the sheets is fluid pervious to allow entry of fluid into the capillary zone.

Another preferred embodiment of the present invention pertains to a capillary laminate material formed by at least two fluid pervious sheet having a capillary zone between the sheets which are held apart by spacer elements.

The capillary laminate material may be formed from more than two sheets such that multiple capillary zones are formed. The top or uppermost sheet and all intermediate sheets are fluid pervious to allow fluid flow between adjacent capillary zones. The bottom or lowermost sheet may be either pervious or impervious to fluid depending on the desired use and/or result.

The spacer elements within the capillary laminate material may be shaped and arranged to divide the capillary zone into capillary channels which direct the flow of fluid within the capillary zone.

The sheets of the capillary laminate material may exist in many forms and may be made from a number of suitable materials. The sheets may be nonwoven webs, films, microporous sheets, porous sheets, etc. The sheets may be made from a number of suitable materials including but not limited to polyolefins, polyester, nylon, elastomers, etc.

The sheets of the capillary laminate material may be rendered fluid pervious by several mechanisms. These include, but are not limited to apertures, porous mediums, microporous mediums, slits, etc. When apertures are used to render the sheet, or sheets, fluid pervious, they can be provided in numerous combinations and patterns to obtain various results. The apertures in a sheet can all be the same size or they can be varied. For example, the sheet may have large apertures near the point of maximum fluid delivery and smaller apertures away from the point of maximum fluid delivery. The frequency of the apertures can also be varied across the surface of the sheet, with a higher frequency in one location than in another location.

The aperture frequency and/or size may also be varied between adjacent sheets within the capillary laminate material to achieve certain desired flow properties. For example, successively smaller apertures in adjacent sheets can be used to create a capillary driving force through the capillary laminate material in is the direction of the smaller apertures.

The spacer elements used to both separate and secure the sheets of the capillary laminate material together can be a single spacer or a plurality of spacers having various geometric shapes. The height of the spacers will determine the gap between the sheets or the capillary zone. The capillary zone can be designed to optimally handle different fluids. For example, it has been determined that for blood or menses, the capillary zone should be about 0.003 inches (3 mils). Water or urine is best transferred by a smaller capillary zone. The capillary zone may be varied throughout the capillary laminate material. Variability of the capillary zone can be used to encourage fluid flow in the direction of decreasing capillary zone.

The spacers used to form the capillary laminate can be formed from a material which is added to the sheets or from one of the sheets themselves. Examples of materials that can be added include, but are not limited to hot melt adhesives, pressure sensitive adhesives, thermoplastics with a melting point temperature lower than one or more of the sheets, etc. These additions materials can be applied by gravure printing, screen printing or any number of processes which are known to those skilled in the art.

Alternatively, the spacers may be formed from one or more of the sheets themselves. This can be achieved by embossing, either hot or cold, casting or other processes known to those skilled in the art.

The spacers may also be used to divide the capillary zone into capillary channels. Capillary channels can be utilized to direct flow within the capillary zone. The capillary channels can be linear, curvilinear or a combination of both. The capillary channels can be uniform in cross-sectional area or they can vary along their length. For example, a decreasing cross-sectional area of a capillary channel can promote fluid flow in the direction of decreasing cross-sectional area.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein:

DETAILED DESCRIPTION OF THE INVENTION

As used herein, the term "absorbent article" refers to devices which absorb and contain body exudates, and more specifically refers to devices which are placed against or in proximity to the body of the wearer to absorb and contain the various exudates discharged from the body. The term "absorbent article" is intended to include diapers, catamenial pads, sanitary napkins, pantiliners, incontinent pads and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
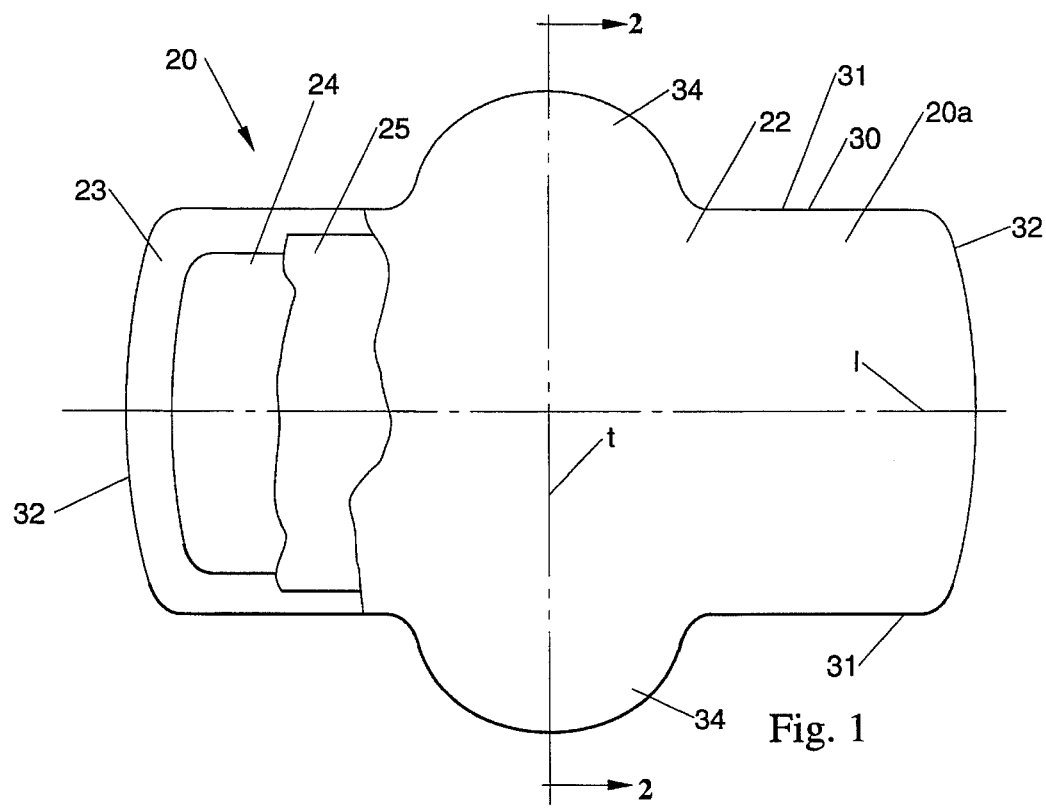
FIG. 1 is a top plan view of a sanitary napkin with portions of the sanitary napkin cut-away to more clearly show the construction of the sanitary napkin.

A preferred embodiment of a unitary disposable absorbent article is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, incontinent pads, and the like.

Sanitary napkin 20 has two surfaces, a wearer-contacting surface or body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portion of the sanitary napkin being cut-away to more clearly show the construction of the sanitary napkin 20 and with the portion of the sanitary napkin 20 which faces or contacts the wearer 20a oriented towards the viewer. As shown in FIG. 1, the sanitary napkin 20 preferably comprises a liquid pervious topsheet 22, a liquid impervious backsheet 23 joined with the topsheet 22, an absorbent core 24 positioned between the top sheet 22 and the backsheet 23, and an acquisition layer 25 positioned between the topsheet 22 and the absorbent core 24.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

The sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
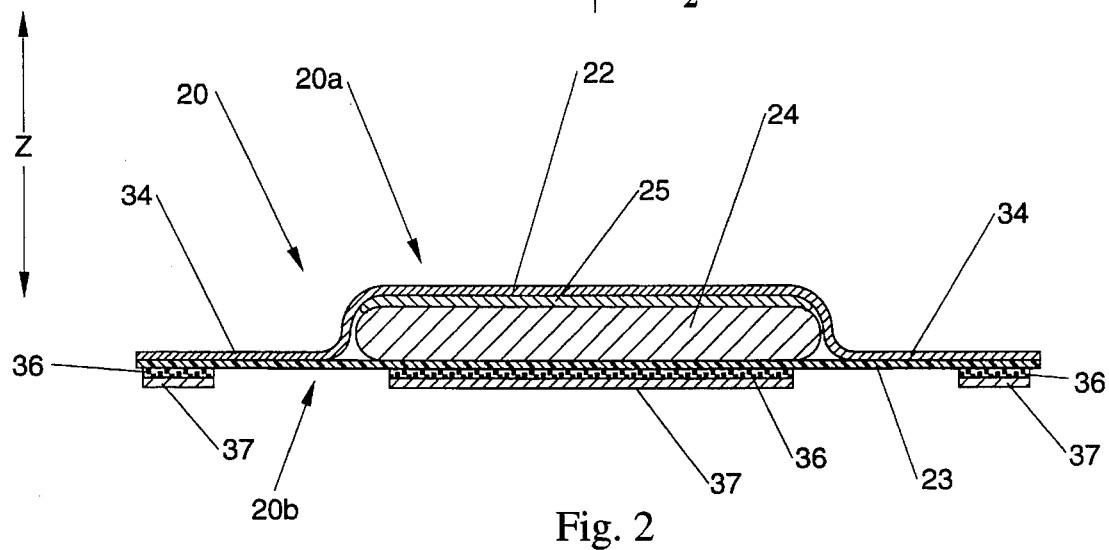
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. As can be seen in FIG. 2 the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "Z" direction or axis, which is the direction proceeding down through the topsheet 22 and into whatever fluid storage core 24 that may be provided. The objective is to provide a continuous path between the topsheet 22 and underlying layer or layers of the absorbent article herein, such that fluid is eventually drawn in the "Z" direction and away from the top sheet of the article and into its ultimate storage layer.

Figure 3:
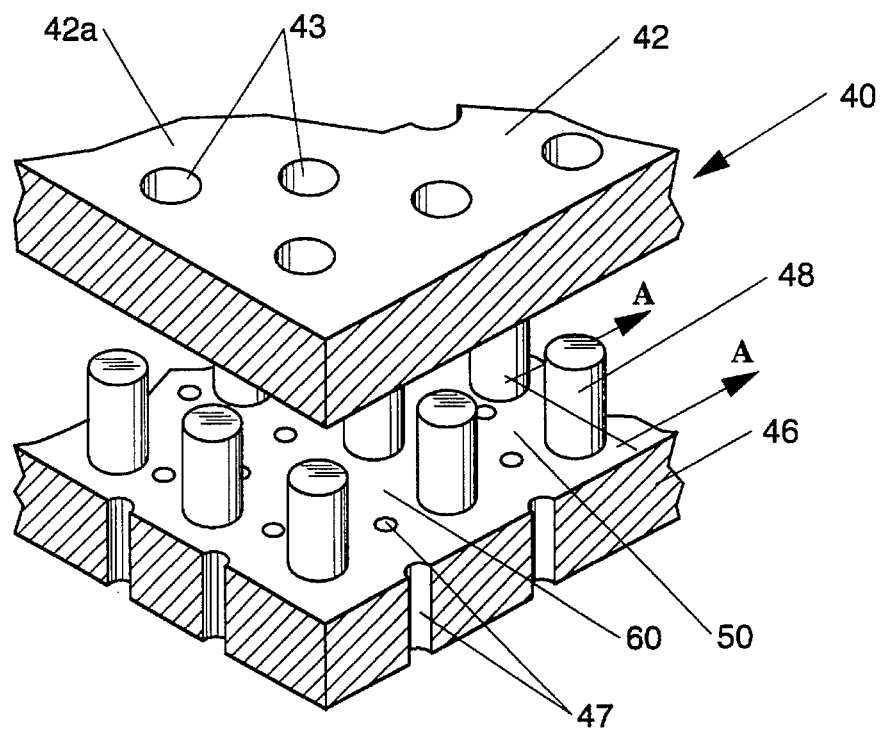
FIG. 3 is a cut-away view of a preferred embodiment of a capillary laminate film of the present invention.
Figure 4:
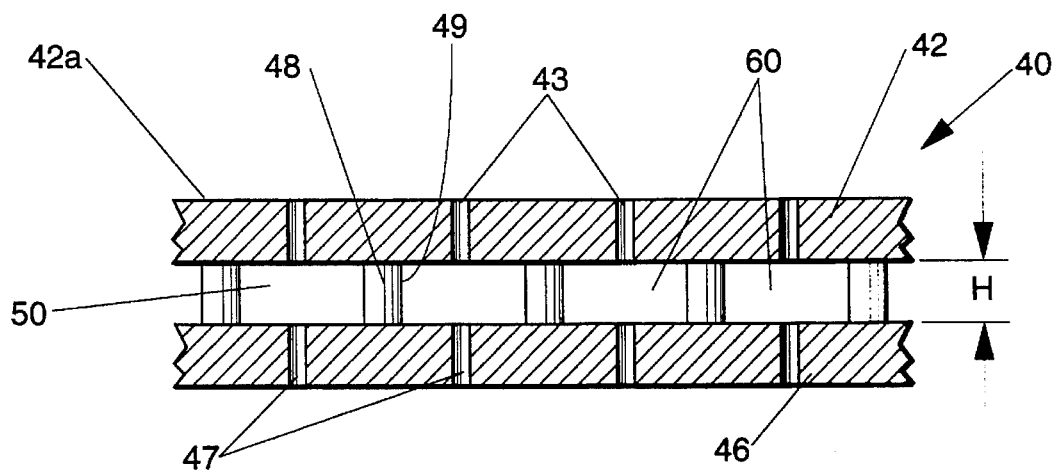
FIG. 4 is a cross-sectional view of the capillary laminate film of FIG. 3.

Referring now to FIGS. 3 and 4 there is shown a capillary laminate material 40 of the present invention. Capillary laminate material 40 is particularly well suited for use as a topsheet 22 or acquisition layer 25 in a sanitary napkin 20 of the type generally illustrated in FIGS. 1 and 2. Capillary laminate material 40 shown in FIGS. 3 and 4 comprises a first fluid pervious sheet or layer 42 and a second fluid pervious sheet or layer 46. The fluid pervious nature of the first sheet 42 and the second sheet 46 is provided by apertures 43 and 47, respectively. While the fluid pervious nature of the first and second sheets 42 and 46 is provided by apertures 43 and 47, it would be obvious to one of ordinary skill in the art that there are other means of imparting a fluid pervious nature to a sheet, such as microporous materials, porous material, slits, etc. The first and second sheets are spaced apart from one another by a spacer. The spacer shown in FIGS. 3 and 4 comprises a plurality of cylindrical spacers 48. Spacers 48 also serve to connect or secure the first sheet 42 to the second sheet 46. Spacers 48 separate first sheet 42 from second sheet 46 such that a "capillary zone" 50 is created between the first sheet 42 and the second sheet 46. As used herein, the term "capillary zone" refers to the space between two adjacent sheets not being occupied by a spacer.

The material selected for the first sheet 42 and the second sheet 46 is preferably machinable and capable of being formed into a sheet. Since the capillary laminate material 40 is to be used in consumer products which contact the human body, the capillary laminate material 40 is preferably soft and safe for epidermal or other human contact. Preferred materials for the first sheet 42 and the second sheet 46 are polymeric materials including, but not limited to polyolefins, particularly polyethylenes, polypropylenes and copolymers having at least one olefinic constituent. Other polymeric materials such as polyester, nylon, copolymers thereof and combinations of any of the foregoing may also be suitable. While first sheet 42 and second sheet 46 are shown as a film, the sheets may, if desired, be in the form of a nonwoven, microporous membrane, foam, etc.

If desired, conventional amounts of agents may also be added to the polymeric matrix of the first sheet 42 and the second sheet 46. It is often desired to add agents to increase the opacity of the sheets. Whiteners, such as titanium dioxide and calcium carbonate may be used to opacify the first and second sheets, 42 and 46, respectively. It may also be desired to add other agents such as surfactants to impart a hydrophilic nature to either the first sheet 42 or the second sheet 46. Degrees and amounts to which agents including whiteners and surfactants are added to the first sheet 42 and the second sheet 46 may be distinct from one another to provide varying effects such as hydrophilicity gradients and the ability to mask fluids within the absorbent article.

The first sheet 42 and the second sheet 46 may themselves be multilayer polymeric films such as those disclosed in commonly assigned U.S. Pat. No. 5,006,394 issued to Baird on Apr. 9, 1991 and U.S. Pat. No. 5,261,899 issued to Visscher et al. on Nov. 16, 1993, said patents being incorporated herein as by reference.

The spacers 48 may be made from any material suitable for securing the first sheet 42 to the second sheet 46. For example, spacers 48 may be made from a heat sealable hot melt adhesive manufactured by Eastman Chemical under the designation Eastobond A3 or a pressure sensitive adhesive such as HL-1258 manufactured by Fuller Adhesive. The spacers 48 may also be made from a polymer material having a lower melting point temperature than the polymeric material used for either the first sheet 42 or the second sheet 46.

The spacers 48 are preferably applied to one of the sheets using a known technique such as gravure printing, screen printing, or transfer printing. When using a pressure sensitive adhesive sufficient pressure must be applied to achieve bonding or securement between the spacers and the respective sheets. When using a hot melt adhesive or a polymeric material having a lower melting point temperature than the materials used for either the first sheet or the second sheet, sufficient heat must be applied to heat the spacers to achieve bonding between the respective sheets.

In another preferred embodiment, the spacers 48 may be formed from one or more of the sheets. The formation may be through embossing either hot or cold, casting or other known techniques. The other sheet is then combined with the embossed or cast sheet to form the laminate material of the present invention.

When used as a topsheet on an absorbent article, such as topsheet 22 on sanitary napkin 20 shown in FIGS. 1 and 2, the first sheet 42 becomes the wearer-contacting or body surface of the topsheet. The second sheet 46 becomes the garment facing or pad-contacting surface of the topsheet. Accordingly, as fluid impinges capillary laminate material 40 it first contacts the wearer-contacting surface 42a of the first sheet 42. Fluid then proceeds through apertures 43 and into the capillary zone 50. Upon reaching capillary zone 50 fluid then moves within the capillary zone 50 under capillary pressure. The fluid moves throughout the capillary zone 50 in both the longitudinal and transverse directions. Simultaneously, the fluid passes through apertures 47 in second sheet 42 and into the acquisition layer 25 of sanitary napkin 20, as shown in FIGS. 1 and 2.

The dimensions of apertures 43 and 47 in first sheet 42 and second sheet 46, respectively, may be substantially identical to one another or may be of different dimensions. When used as a topsheet or an acquisition layer, it may be desirable to have apertures 43 slightly larger than apertures 47 to provide a capillary gradient within capillary laminate material 40. It may also be desirable to vary the dimension of the apertures 43 and 47 within their respective sheets. For example, when used as a topsheet it may be desirable to have the apertures 43 in first sheet 42 which are located in the central region of the sanitary napkin, i.e., the region surrounding the intersection of the longitudinal and transverse centerlines, larger than the apertures adjacent the periphery 30 of the sanitary napkin. The difference in dimension may be easily defined from one region to the next, or may be indiscernible as the dimensions may change gradually from one region to the next region.

In addition to varying the size of apertures 43 and 47 it is also possible to vary the frequency of apertures 43 and 47. For example, when used as a topsheet it may be desirable to have a relatively high frequency of apertures near the central region as compared to the regions near the periphery of the absorbent article. In general, the fewer the apertures and the smaller the apertures the larger the capillary zone defined by the two sheets and the spacers.

The dimension of the capillary zone 50 may be also be varied for particular uses. For example, if used as a topsheet on a disposable diaper, the dimension of capillary zone 50 may be smaller than if used as a topsheet on a sanitary napkin, due to the viscosity and density differences of urine and menses and/or blood. Therefore, the capillary zone for a diaper topsheet will more than likely be smaller than the capillary zone of a sanitary napkin topsheet.

The frequency, cross-sectional area, and height of spacers 48 determine to a substantial degree the dimension of the capillary zone 50. The spacers 48 have a height dimension indicated by the letter "H" in FIG. 4. The cross-sectional area of the spacers 48 is determined by taking the cross-sectional area of the spacers in a plane substantially parallel to the first and second sheets 42 and 46, respectively, as is indicated by sectional lines A—A in FIG. 3. Spacers 48 are shown as having a circular cross-sectional shape, however, other cross-sectional shapes such as squares, rectangles, ovals, triangles, arcs, dog bone, etc. may also be used for spacers 48.

The sidewalls 49 of spacers 48 are shown as being substantially straight along their length in FIGS. 3 and 4. However, sidewalls 49 may be concave or convex or any other shape such as sloped, curvilinear, etc. as may be desired.

Within capillary zone 50 there is at least one and more preferably a multiplicity of capillary channels, generally designated as 60. Referring now to FIG. 3, as fluid moves between adjacent spacers 48 the shape of the capillary channel 60 between spacers 48 continually changes. Accordingly, the capillary channels 60 have a non uniform shape along their length.

Figure 5:
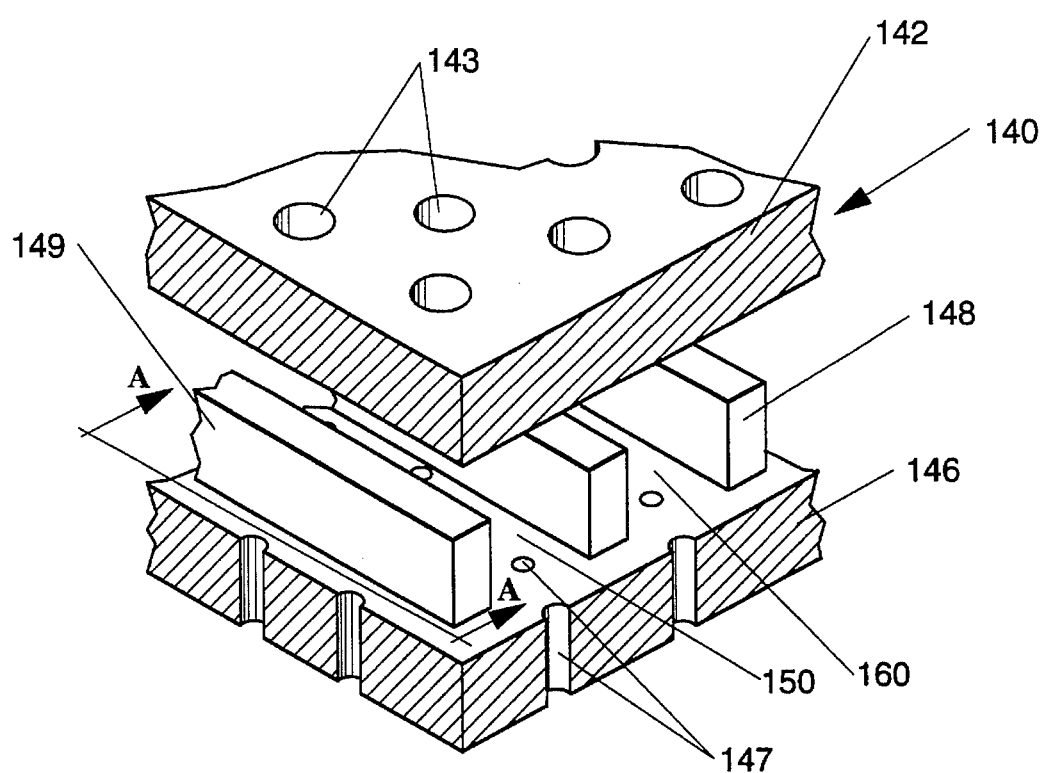
FIG. 5 is a cut-away view of another preferred embodiment of a capillary laminate film of the present invention.

Referring now to FIG. 5 there is shown another embodiment of a capillary laminate material 140 of the present invention. Capillary laminate material 140 comprises a first fluid pervious sheet 142 having a plurality of apertures 143 therein and a second fluid pervious sheet 146 having a plurality of apertures 147 therein. The first and second sheets are spaced apart from one another by a plurality of spacers 148. Spacers 148 have a substantially rectangular cross-section when taken along section line A—A. The sidewalls 149 of spacers 148 are substantially straight. Spaces 148 also serve to connect the first sheet 142 to the second sheet 146. Spacers 148 separate first sheet 142 from second sheet 146 such that a capillary zone 150 is created between the first and second sheets. The capillary zone 150 is divided into a plurality of capillary channels 160. As spacers 148 are aligned substantially parallel to one another, the capillary channels 160 are substantially straight along their entire length.

The capillary channels within the capillary zone may take on any shape as desired. For example, the capillary channels may be straight along their entire length, straight along only a portion of their length, continuous along their entire length, discontinuous along their entire length, curvilinear, extend in a fan-like array, oval, hourglass, dog bone, asymmetric, etc.

Figure 6:
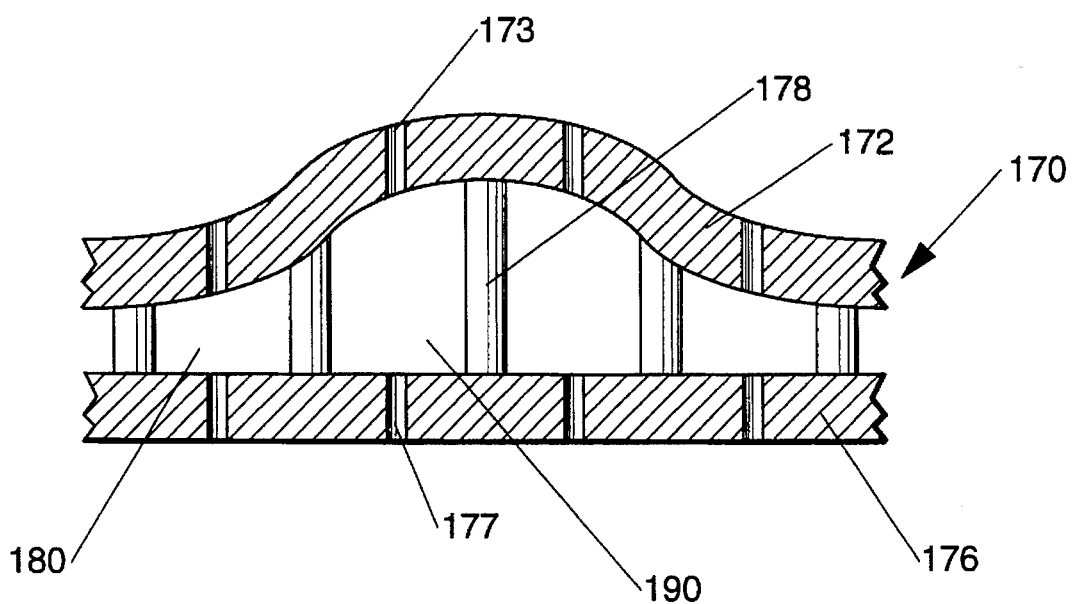
FIG. 6 is a cross-sectional view of another preferred embodiment of a capillary laminate film of the present invention.

In FIG. 6 there is shown another embodiment of a capillary laminate material 170 of the present invention. Capillary laminate material 170 is particularly well suited for use as a topsheet on an absorbent article, such as sanitary napkin 20 in FIG. 1. Capillary laminate material 170 includes a first sheet 172 having a plurality of apertures 173 therein and a second sheet 176 having a plurality of apertures 177 therein. First sheet 172 and second sheet 176 are spaced apart from one another by a plurality of spacers 178 to define a capillary zone 180 between the first and second sheets. Within the capillary zone 180 there are a plurality of capillary channels 190. The dimension of the capillary zone 180 is substantially non uniform throughout the capillary laminate material as compared to the capillary laminate material 140 in FIG. 5 which has a substantially uniform capillary zone 150.

Figure 7:
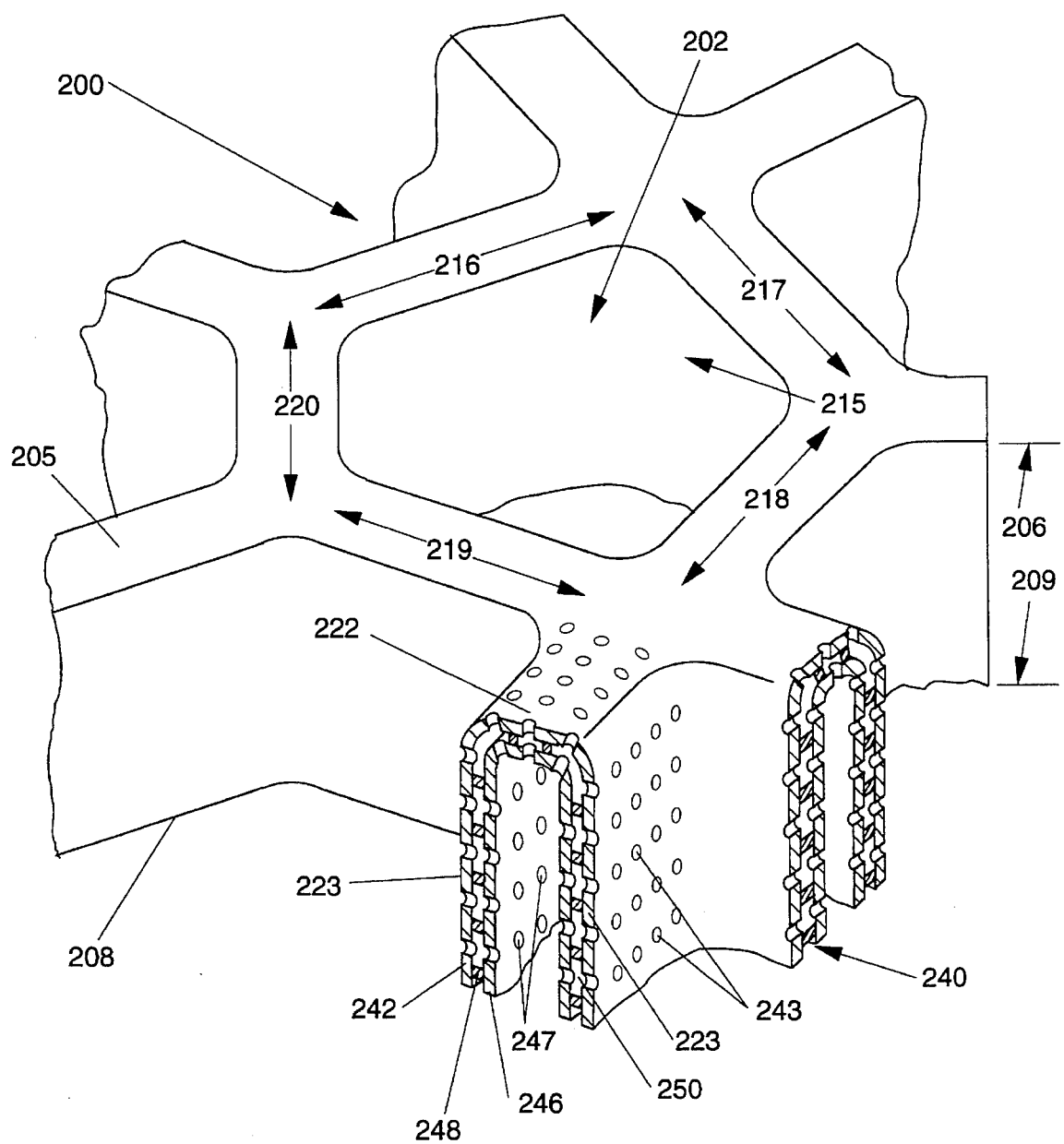
FIG. 7 is an enlarged, partially segmented, perspective illustration of a preferred embodiment of the capillary laminate film of FIG. 3, having been formed into a three-dimensional, macroscopically expanded, apertured, web of the type generally disclosed in U.S. Pat. No. 4,342,314.

FIG. 7 is an enlarged, partially segmented, perspective illustration of another preferred embodiment of the capillary laminate film of FIG. 3, which has been formed into a macroscopically expanded, three-dimensional, fiber-like, apertured web 200. The macroscopically expanded web 200 is generally in accordance with the teachings of commonly assigned U.S. Pat. No. 4,342,314 issued to Radel et al. on Aug. 3, 1982 and hereby incorporated herein by reference. Web 200 has been found suitable for use as a topsheet 22 on sanitary napkin 20. The term "macroscopically expanded", when used to describe three-dimensional webs of the present invention, refers to webs, ribbons, and films which have been caused to conform to the surface of a three-dimensional forming structure so that both surfaces thereof exhibit a three-dimensional pattern of surface aberrations corresponding to the macroscopic cross-section of said forming structure. The surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plane of the web is about 12 inches. The term "fiber-like" as utilized herein to describe the appearance of webs of the present invention, refers generally to any fine-scale pattern of apertures, random or non-random, reticulated or non-reticulated, which connotes an overall appearance and impression of a woven or non-woven fibrous web when viewed by the human eye. As can be seen in FIG. 7, the webs fiber-like appearance is comprised of a continuum of fiber-like elements, the opposed ends of each of the fiber-like elements are interconnected to at least one other of the fiber-like elements. In the embodiment disclosed in FIG. 7, the interconnected fiber-like elements form a pattern network of pentagonally shaped capillaries 202. The web 200, which exhibits a fiber-like appearance, embodies a three-dimensional microstructure extending from the web's uppermost or wearer-contacting surface 205 in plane 206 to its lowermost or absorbent pad-contacting surface 208 in plane 209 to promote rapid fluid transport from the uppermost surface 205 to the lowermost surface 208 of the web without lateral transmission of fluid between adjacent capillaries 202. As utilized herein, the term "microstructure" refers to a structure of such fine scale that its precise detail is readily perceived by the human eye only upon magnification by a microscope or other means well-known in the art.

Apertures 215 are formed by a multiplicity of intersecting fiber-like elements, e.g., elements 216, 217, 218, 219 and 220, interconnected to one another in the first surface of the web. Each fiber-like element comprises a base portion, e.g., base portion 222, located in plane 206. Each base portion has a sidewall portion, e.g., sidewall portions 223, attached to each edge thereof. The sidewall portions 223 extend generally in the direction of the second surface 208 of the web. The intersecting sidewall portions of the fiber-like elements are interconnected to one another intermediate the first and the second surfaces of the web and terminate substantially concurrently with one another in the plane 209 of the second surface.

In a particularly preferred embodiment, the interconnected sidewall portions terminate substantially concurrently with one another in the plane of the second surface to form apertures 225 in the second surface 208 of the web. The network of capillaries 202 formed by the interconnected sidewall portions allows for free transfer of fluid from the first surface of the web directly to the second surface of the web without lateral transmission of the fluid between the adjacent capillaries.

In addition, small amounts of fluid are able to penetrate the apertures 243 in the first layer 242 of the capillary laminate material 240. The first layer 242 is separated from and secured to the second layer 246 by spacers 248 to provide a capillary zone 250 between the first and second sheets. After penetrating apertures 243, fluid will then move through the capillary zone 250 toward the second surface of the web. Upon reaching the second surface of the web, fluid will be removed from the capillary zone 250 and transmitted to the underlying layer. Fluid may also enter apertures 247 in the second layer 246.

The absorbent core 24 may be any absorbent means which is capable of absorbing or retaining liquids (e.g., menses and/or urine). As shown in FIGS. 1 and 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as creped polyester fibers; peat moss; tissue including tissue wraps and tissue laminates; absorbent foams; absorbent sponges; superabsorbent polymers; absorbent gelling material; or any equivalent material or combinations of material, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; U.S. Pat. No. 5,009,653 issued to Osborn on Apr. 23, 1991; and European Patent Application No. 0 198 683, The Procter & Gamble Company, published Oct. 22, 1986 in the name of Duenk et al. Each of these patents are incorporated herein by reference.

Alternatively, the absorbent core 24 may comprise a laminate structure comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et al. on Dec. 19, 1989; U.S. Pat. No. 4,822,543 issued to Dean et al. on Apr. 18, 1989; U.S. Pat. No. 4,889,595 is issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The laminate may be formed of a sheet of cross-linked cellulosic fibers that wraps the layer of particles of absorbent gelling material. The sheet is wrapped so that it appears as having a "c" configuration when viewed from the end. The wrapped sheet forms an upper layer and a lower layer. In alternative as embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable cured, chemically stiffened cellulosic fibers from which one can prepare the refined, cured, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other cross-linked cellulosic fibers are also known, and such fibers may also be used herein, although the fluid absorbency properties may be suboptimal as compared with the above-mentioned fibers. Reference can be made to the various citations in U.S. Pat. 4,898,642 and PCT U.S. 89 01581 for other fibers used to prepare the preferred absorbent cores used in the practice of this invention.

Alternatively, the absorbent core 24 may comprise a capillary laminate material. When used as an absorbent core the dimension and frequency of the apertures in the first and second sheets, and the dimension, height and frequency of spacers may be somewhat different than those of a capillary laminate material which is used as a topsheet. For example, the capillary zones may be somewhat larger to enable the capillary laminate material to hold greater amounts of fluid.

Absorbent gelling materials may be spread around the lateral and transverse edges of the capillary laminate material to hold fluid within the capillary laminate material. Alternatively, the capillary laminate material may be used as a portion of an absorbent core wherein the capillary laminate material is positioned onto a bed or layer of absorbent gelling materials or superabsorbents.

Figure 8:
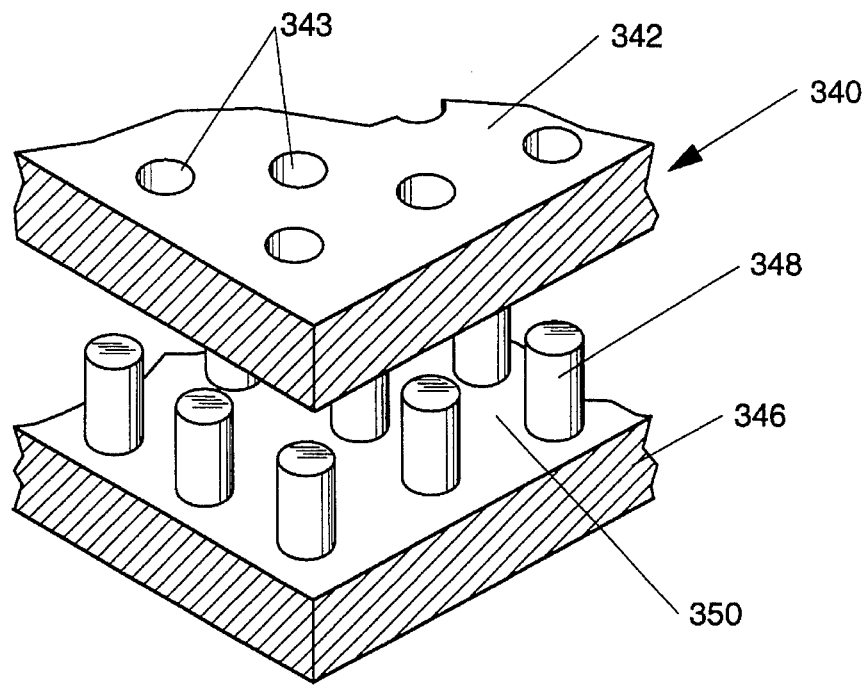
FIG. 8 is a cut-away view of another preferred embodiment of a capillary laminate film of the present invention.
Figure 9:
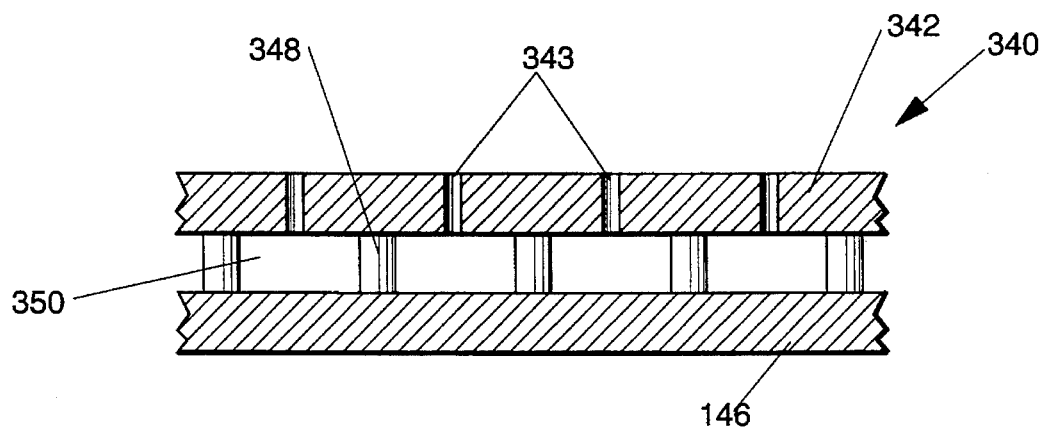
FIG. 9 is a cross-sectional view of the capillary laminate film of FIG. 8.

In FIGS. 8 and 9 there is shown another preferred embodiment of a capillary laminate material 340 of the present invention. Capillary laminate material 340 comprises a first sheet 342 and a second sheet 346 secured together and spaced apart by a plurality of spacers 348. First sheet 342 includes a plurality of apertures 343. The second sheet 346 is substantially non-apertured, thus preventing fluids to transmit therethrough. Capillary laminate material 340 may be particularly useful as a macroscopically expanded topsheet such as that shown in FIG. 7 where it is not desired or necessary to have fluid penetrate the second sheet 346. Alternatively, the capillary laminate material 340 may also be used as an absorbent core wherein the second sheet 346 is impervious to liquids and therefore may aid the backsheet in the protection against soiling of undergarments and clothing.

Figure 10:
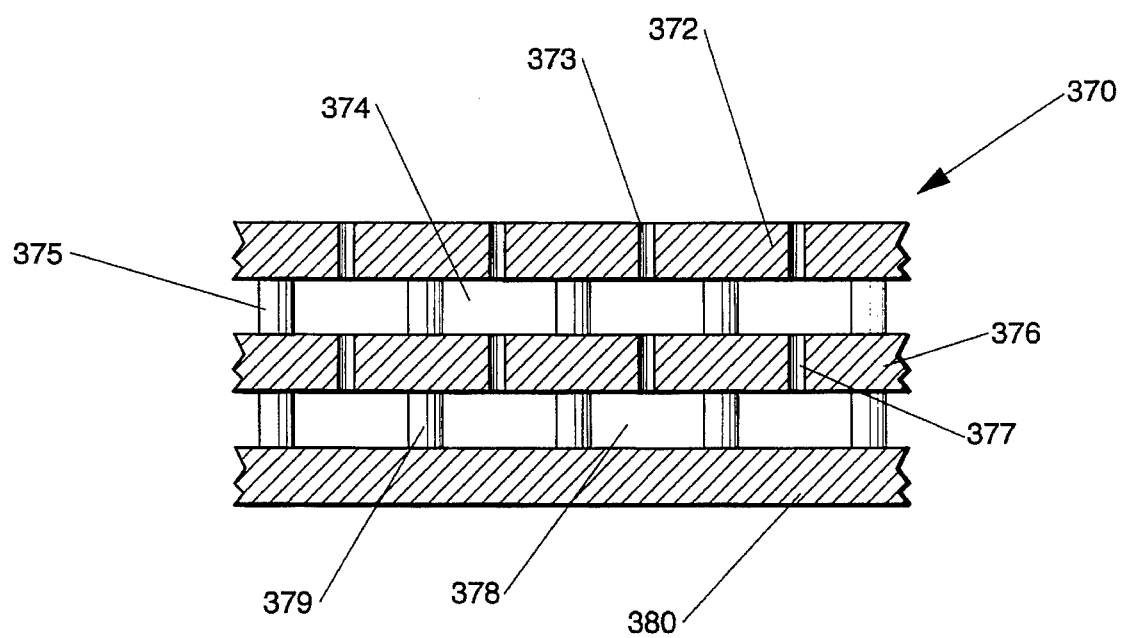
FIG. 10 is a cross-sectional view of another preferred embodiment of a capillary laminate film of the present invention.

In FIG. 10 there is shown another preferred embodiment of a capillary laminate material 370 of the present invention. Capillary laminate material 370 includes a first sheet 372 secured to a second sheet 376 by a plurality of spacers 375. Sheet 372 has a plurality of apertures 373 therein. Second sheet 376 has a plurality of apertures 377. A capillary zone 374 is provided between the first sheet 372 and the second sheet 376. Capillary laminate material 370 also includes a third sheet 380 secured to second sheet 376 by spacers 379. A capillary zone 378 is provided between the second sheet 376 and the third sheet 380. Third sheet 380 preferably has no apertures therein.

Capillary laminate material 370 may be formed into a macroscopically s expanded web similar to that shown in FIG. 7. Preferably, the capillary laminate material 370 will be used as an absorbent core in an absorbent article. By increasing the layers of the capillary laminate film, the capillary laminate film is able to hold and store more fluid. The particular number of layers is limitless and may be designed to handle the projected volumes of fluid.

The backsheet 23 is impervious to liquids (e.g., menses and/or urine) and is preferably manufactured form a thin plastic film, although other flexible liquid impervious material may also be used. As used herein, the term "flexible" refers to material which are compliant and will readily conform to the general shape and contours of the human body. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P 18-0401 and by Ethyl Corporation, Visqueen Division, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305 -IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox El/0 and BL30MG-A Silox 4P/0 both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs.

The flaps 34 serve at least two purposes. First, the flaps 34 help serve to prevent soiling of the wearer's body and panties by menstrual fluid, preferably by forming a double wall barrier along the edges of the panties. Second, the flaps 34 are preferably provided with attachment means on their garments surface so that the flaps 34 can be folded back under the panty and attach to garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 (i.e., unitary).

A number of sanitary napkins having flaps suitable or adaptable for use with the sanitary napkins of the present invention are disclosed in U.S. Pat. No. 4,687,478 entitled "Shaped Sanitary Napkin With Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Medingly on Aug. 26, 1986.

In a preferred embodiment of the present invention, an acquisition layer(s) may be positioned between the topsheet and the absorbent core. The acquisition layer may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

Alternatively, the acquisition layer may comprise a capillary laminate material. When used as an acquisition layer core the dimension and frequency of the apertures in the first and second sheets, and the dimension, height and frequency of the spacers may be somewhat different than those of a capillary laminate material which is used as a topsheet or an absorbent core.

While particular embodiments of the present invention have been illustrated and described, it would be obvious to one skilled in the art that there is other changes and modifications that can be made without departing from the spirit and scope of the present invention. It is therefore intended to cover in the appended claims all such changes and modifications that are within the scope of this invention.

What is claimed is:

1. A laminate material comprising:
    a first sheet and a second sheet, said first sheet being fluid pervious, said first sheet and said second sheet being spaced apart from one another by at least one spacer to define a capillary zone therebetween for the capillary movement of fluid, said spacer connecting said first sheet and said second sheet together to form said laminate material, said spacer maintaining said first sheet and said second sheet at a dimensional spacing sufficient to impart capillary forces to a fluid entering said capillary zone and move said fluid within said capillary zone via capillary pressure.

2. The laminate material of claim 1, wherein said second sheet is fluid impervious.

3. The laminate material of claim 1, wherein said second sheet is fluid pervious.

4. The laminate material of claim 1, wherein said first sheet includes a plurality of apertures.

5. The laminate material of claim 4, wherein said second sheet includes a plurality of apertures.

6. The laminate material of claim 5, wherein said apertures in said first sheet are larger than said apertures in said second sheet.

7. The laminate material of claim 5, wherein said first sheet and said second sheet are comprised of a polymeric material.

8. The laminate material of claim 1, wherein said capillary zone is divided into a plurality of capillary channels by said spacer.

9. The laminate material of claim 8, wherein said channels have a substantially non uniform shape along their length.

10. The laminate material of claim 8, wherein said channels have a substantially uniform shape along their length.

11. The laminate material of claim 8, wherein said channels are substantially straight along a portion of their length.

12. The laminate material of claim 8, wherein said channels are substantially straight along their entire length.

13. The laminate material of claim 8, wherein said channels are curvilinear.

14. The laminate material of claim 1, wherein said capillary zone has a substantially uniform dimension throughout said laminate material.

15. The laminate material of claim 1, wherein said capillary zone has a substantially non uniform dimension throughout said laminate material.

16. The laminate material of claim 1, wherein said spacers are formed from said first sheet.

17. The laminate material of claim 1, wherein said spacers are formed from said second sheet.

18. A laminate material comprising:
    a first sheet having a plurality of apertures therein and a second sheet having a plurality of apertures therein, said first sheet and said second sheet being spaced apart from one another by a plurality of spacers to define a capillary zone therebetween for the capillary movement of fluid, at least one of said spacers connecting said first sheet and said second sheet together to form said laminate material, said spacers maintaining said first sheet and said second sheet at a dimensional spacing sufficient to impart capillary forces to a fluid entering said capillary zone and move said fluid within said capillary zone via capillary pressure.

19. The laminate material of claim 18, wherein said apertures in said first sheet are larger than said apertures in said second sheet.

20. The laminate material of claim 18, wherein said first sheet and said second sheet are comprised of a polymeric material.

21. The laminate material of claim 18, wherein substantially all of said spacers connect said first sheet and said second sheet together.

22. The laminate material of claim 18, wherein said capillary zone is divided into a plurality of capillary channels by said spacers.

23. The laminate material of claim 22, wherein said channels have a substantially non uniform shape along their length.

24. The laminate material of claim 22, wherein said channels have a substantially uniform shape along their length.

25. The laminate material of claim 22, wherein said channels are substantially straight along a portion of their length.

26. The laminate material of claim 22, wherein said channels are substantially straight along their entire length.

27. The laminate material of claim 22, wherein said channels are curvilinear.

28. The laminate material of claim 22, wherein said laminate material is an absorbent element in an absorbent article.

29. The laminate material of claim 18, wherein said capillary zone has a substantially uniform dimension throughout said laminate material.

30. The laminate material of claim 18, wherein said capillary zone has a substantially non uniform dimension throughout said laminate material.

31. A laminate material comprising:
at least two fluid pervious sheets being spaced apart from one another by a plurality of spacers to define a capillary zone therebetween for the capillary movement of fluid, said spacers connecting said fluid pervious sheets together, said spacers maintaining said fluid pervious sheets at a dimensional spacing sufficient to impart capillary forces to a fluid entering said capillary zone and move said fluid within said capillary zone via capillary pressure, said laminate material further comprising a fluid impervious sheet spaced apart from one of said fluid pervious sheets by a plurality of spacers to define a secondary zone therebetween for the movement of fluid, at least one of said spacers connecting one of said fluid pervious sheets to said fluid impervious sheet to form a laminate material.

32. The laminate material of claim 31, wherein said fluid pervious sheets include a plurality of apertures.

33. The laminate material of claim 31, wherein said fluid pervious sheets are comprised of a polymeric material.

34. The laminate material of claim 31, wherein said fluid impervious sheet is comprised of a polymeric material.

35. The laminate material of claim 31, wherein said secondary zone is a capillary zone and wherein said spacers maintain said fluid impervious sheet and said one of said fluid pervious sheets at a dimensional spacing sufficient to impart capillary forces to a fluid entering said capillary zone and move said fluid within said capillary zone via capillary pressure.

36. The laminate material of claim 35, wherein said capillary zone is divided into a plurality of capillary channels by said spacers.

37. The laminate material of claim 36, wherein said channels have a substantially non uniform shape along their length.

38. The laminate material of claim 36, wherein said channels have a substantially uniform shape along their length.

39. The laminate material of claim 36, wherein said channels are substantially straight along a portion of their length.

40. The laminate material of claim 36, wherein said channels are substantially straight along their entire length.

41. The laminate material of claim 36, wherein said channels are curvilinear.

42. An absorbent article including a wearer-contacting topsheet and an absorbent element for absorbing body fluids, said topsheet comprising: a laminate material including a first sheet and a second sheet, said first sheet having a plurality of apertures therein, said second sheet having a plurality of apertures therein, said first sheet and said second sheet being spaced apart from one another by a plurality of spacers to define a capillary zone therebetween for the capillary movement of fluid, at least one of said spacers connecting said first sheet and said second sheet together to form said laminate material, said spacers maintaining said first sheet and said second sheet at a dimensional spacing sufficient to impart capillary forces to a fluid entering said capillary zone and move said fluid within said capillary zone via capillary pressure.

43. The absorbent article of claim 42, further including a backsheet secured to said topsheet, said backsheet being resistant to the passage of fluid therethrough.

44. The absorbent article of claim 42, wherein said laminate material is formed into a three-dimensional, macroscopically expanded, apertured web.

45. The absorbent article of claim 42, wherein said absorbent article is a disposable diaper.

46. The absorbent article of claim 42, wherein said absorbent article is a sanitary napkin.

47. An absorbent article including a wearer-contacting topsheet and an absorbent element for absorbing bodily fluids, said absorbent element comprising: a laminate material including a first sheet and a second sheet, said first sheet having a plurality of apertures therein, said first sheet and said second sheet being spaced apart from one another by a plurality of spacers to define a capillary zone therebetween for the capillary movement of fluid, at least one of said spacers connecting said first sheet and said second sheet together to form said laminate material, said spacers maintaining said first sheet and said second sheet at a dimensional spacing sufficient to impart capillary forces to a fluid entering said capillary zone and move said fluid within said capillary zone via capillary pressure.

* * * * *